United States Patent [19]

Scott

[11] 4,098,268

[45] Jul. 4, 1978

[54] WATER IMPERVIOUS COVER FOR AN ARM CAST OR LEG CAST

[76] Inventor: Dalbert Byron Scott, 3201 Vista Cielo La., Spring Valley, Calif. 92077

[21] Appl. No.: 757,317

[22] Filed: Jan. 6, 1977

[51] Int. Cl.² ............................................. A61F 13/00
[52] U.S. Cl. ............................. 128/82; 128/DIG. 20
[58] Field of Search ................... 128/82, 83, DIG. 20, 128/402, 403, 165

[56] References Cited

U.S. PATENT DOCUMENTS

| 3,083,708 | 4/1963 | Gottfried | 128/DIG. 20 |
| 3,580,248 | 5/1971 | Larson | 128/89 R |
| 3,741,203 | 6/1973 | Liman | 128/82 |
| 3,785,374 | 1/1974 | Lipson | 128/82 |

Primary Examiner—John D. Yasko
Attorney, Agent, or Firm—Brown & Martin

[57] ABSTRACT

A flexible, water impervious shell is shaped to fit over a portion of a person's arm or leg that is secured in a cast and to extend beyond the cast. The shell has a closed end that is shaped to fit over the extremity of the arm or leg, and an open end opposite thereto. When the shell is tightly secured to the skin of the arm or leg at the open end, a pressure seal is created between the shell and the skin at the open end of the shell. An inflation valve communicating through the shell enables the air pressure inside the shell when the shell is fitted over the arm or leg and the open end is tightly secured to the skin, to be increased to thereby reinforce the pressure seal. The exterior surface of the water impervious material of the shell is covered with a fabric, such as nylon, for providing resistance to slippage when the exterior of the cover is wet, except that the exterior region of the water impervious material of the shell near the open end is not covered by fabric. The uncovered water impervious material surface near the open end better grips a strap, which may be wrapped around the shell in the uncovered region to tightly secure the shell to the skin at the open end of the shell, and thereby better holds the strap in place, than would the fabric material which covers the remaining exterior region of the shell.

8 Claims, 4 Drawing Figures

U.S. Patent  July 4, 1978  4,098,268
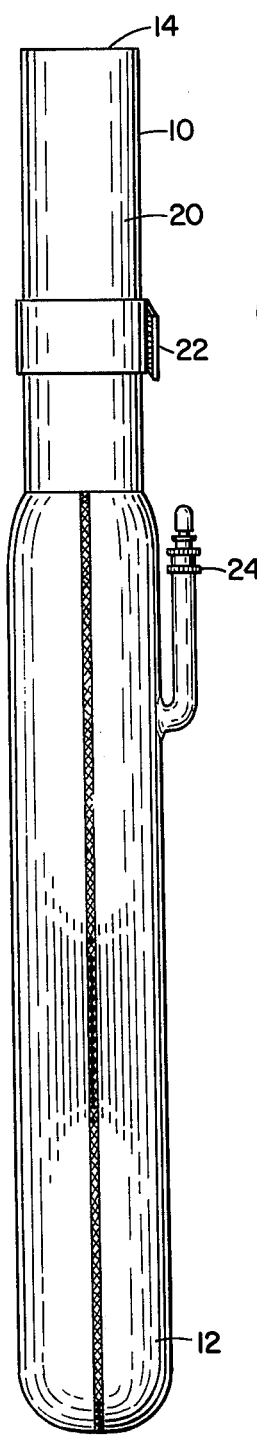
FIG. 2
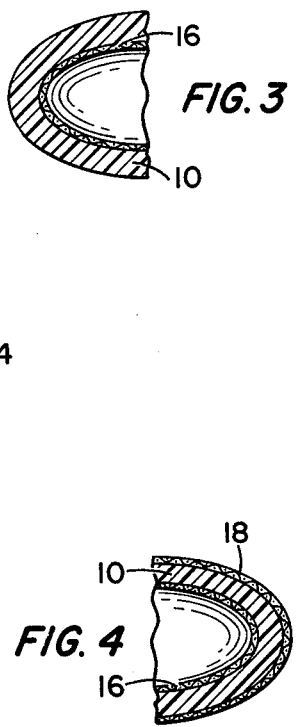
FIG. 3
FIG. 4
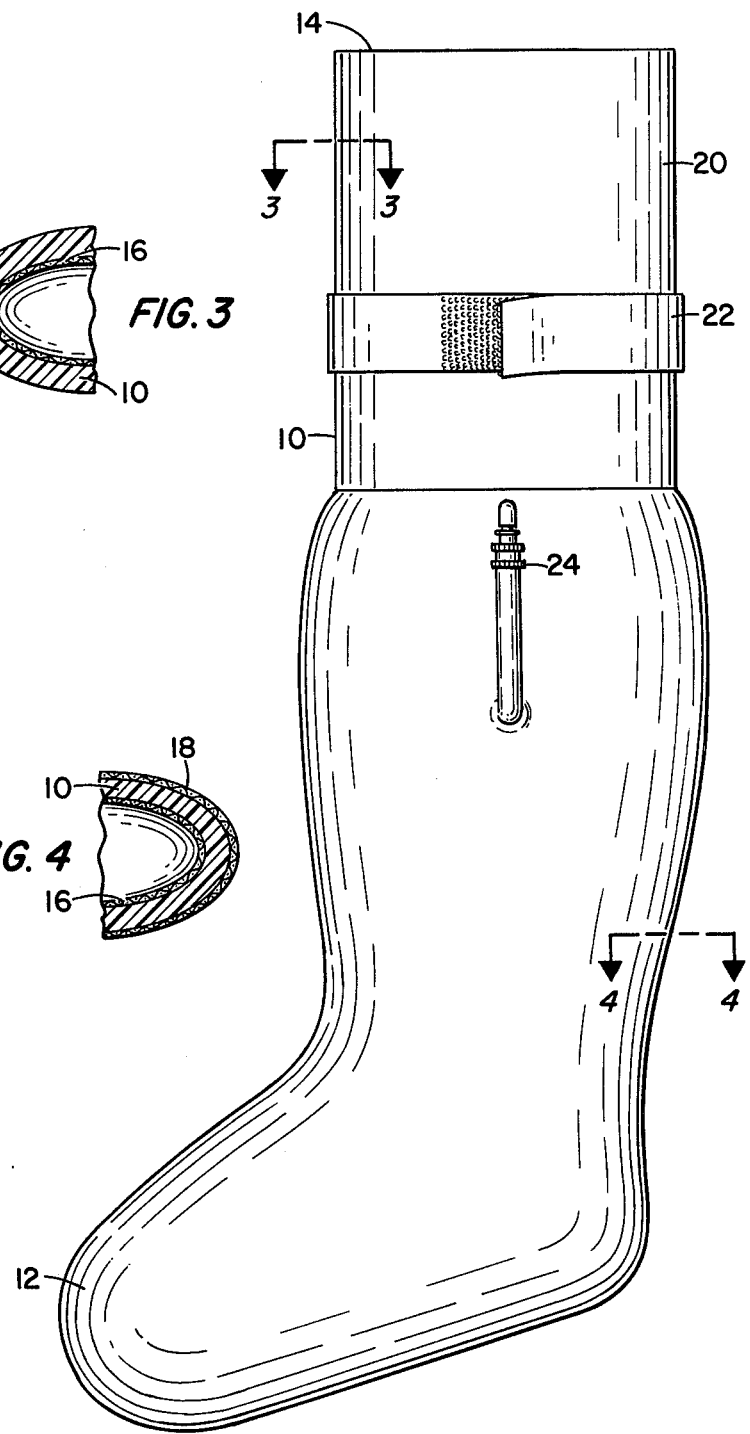
FIG. 1

WATER IMPERVIOUS COVER FOR AN ARM CAST OR LEG CAST

BACKGROUND OF THE INVENTION

The present invention generally pertains to orthopedic aids and is particularly directed to a water impervious cover for an arm cast or leg cast so as to keep the cast dry even though the arm or leg is totally submerged in water.

One of the first things that a patient who has just had his arm or leg placed in plaster cast hears is, "Don't get your cast wet." This is because water will cause the cast to deteriorate. As a result a person having a cast secured to his or her arm or leg is greatly inconvenienced when performing such activities as bathing, showering, or swimming.

Such patients have tried to get around this problem, by using such contrivances as covering the cast with waterproof plastic bags with the open end of the bag being secured to the skin of the arm or leg above the cast with rubber bands. This solution has not proven very satisfactory. Plastic bags are not very durable, and they are slippery so as to provide an additional hazard to a person whose mobility is already impeded by the cast. Also, the shape of a plastic bag is so much different than the shape of an arm or leg, that its fit over the arm or leg is sloppy, and it thereby provides appreciable drag resistance to a patient endeavoring to swim with a plastic bag covering his or her cast.

While a typical rubber boot can be used to cover a leg cast, it does not readily fit over an arm cast. Also, unless a hip boot is used, only a cast covering only a lower portion of the leg, such as the foot and/or ankle, could be covered by the boot. A hip boot is heavy; and it is difficult to swim with a hip boot on one's leg.

In addition it is difficult to provide a great enough pressure seal at the open end of a typical rubber boot so as to keep water from entering the open end when the leg is totally submerged in water, such as during swimming, or bathing in a tub, or soaking in a jacuzzi.

SUMMARY OF THE INVENTION

The present invention is a sheet consisting of a water impervious cover for an arm cast or leg cast. The cover includes a shell consisting of a flexible, waterproof material that is shaped to fit over a portion of an arm or leg that has a cast secured thereto. The shell has a closed end that is shaped to fit over the extremity of the arm or leg and has a open end opposite thereto. When the open end of the shell is extended beyond the cast and the shell is tightly secured to the skin or the arm or leg beyond the cast, a pressure seal is created between the shell and said skin. The waterproof cover also includes an inflation valve communicating through the shell. When the shell is fitted over the arm or leg and the shell is tightly secured to the skin beyond the cast, the inflation valve enables the air pressure inside the shell to be increased to thereby reinforce the pressure seal.

Also, the exterior surface of the water impervious material of the shell is covered with a fabric, such as nylon, for providing resistance to slippage when the exterior of the cover is wet. However, the exterior region of the water impervious material of the shell near the open end preferably is not covered by fabric. Accordingly, the uncovered water impervious material surface near the open end better grips a strap, which preferably is wrapped around the shell in the uncovered region to tightly secure the shell to the skin at the open end of the shell and thereby better holds the strap in place, than would the fabric material which perferably covers the remaining exterior region of the shell.

Preferably the water impervious material is a durable lightweight material such as polymerized chloroprene foam.

Preferably, a strap is wrapped around the shell near the open end to tightly secure the shell to the skin at the open end.

In addition, the interior surface of the water impervious material of the shell preferably is covered with a fabric such as nylon, for facilitating movement of the shell in relation to the arm or leg and the cast.

The water impervious cover of the present invention thus allows a patient wearing an arm or leg cast to freely submerge such arm of leg in water without getting the cast wet. The water impervious cover is durable and lightweight and thereby allows the patient to engage in vigorous water exercises such as swimming.

BRIEF DESCRIPTION OF THE DRAWING

FIG. 1 is a side elevation view of the water impervious cast cover of the present invention.

FIG. 2 is a front elevation view of the cast cover shown in FIG. 1.

FIG. 3 is a sectional view taken along line 3—3 of FIG. 1.

FIG. 4 is a sectional view taken along line 4—4 of FIG. 1.

DESCRIPTION OF THE PREFERRED EMBODIMENT

A water impervious cover for a leg cast according to the present invention is shown in FIGS. 1 to 4.

The cover includes a shell 10 consisting of a water impervious material. The preferred water impervious material is polymerized chloroprene foam, which is sometimes referred to as Neoprene. This water impervious material is flexible, lightweight and durable. It does not tear easily.

The shell 10 is shaped to fit over a persons leg that is secured in a cast. The shell 10 is long enough to extend beyond the cast by about 2 inches (5 cm.). If the cast is above the knee, there must be about 4 or 5 inches of thigh area from the groin to the top of the cast to make room for a proper seal between the shell 10 and the skin beyond the cast.

The shell 10 has a closed end 12 that is shaped to fit over a person's foot. The opposite end 14 of the shell 10 is open.

A layer of nylon fabric 16 is bonded to the entire interior surface of the shell 10. A layer of nylon fabric 18 is also bonded to the exterior surface of the shell 10. However, the region 20 of the exterior surface of the shell 10 at the open end 14 is not covered.

To put the cover on over the cast, the open end 14 is folded back and the cover is slid on easily, just like a stocking.

A strap 22 is wrapped around the uncovered region 20 of the shell 10 to provide a pressure seal between the shell 10 and the skin beyond the cast. The strap is made of Velcro hook and fabric fastener material, which can readily be adjusted to tightly secure the shell 10 to the skin.

The open end 14 of the shell 10 is folded back in the uncovered region 20 to further tighten the pressure seal.

The cover includes an inflation valve 24 which communicates through the shell 10. A small amount of air is added through the inflation valve to increase the air pressure inside the shell 10 and thereby reinforce the pressure seal between the shell 10 and the skin beyond the cast. The air added to the inside of the cover also makes the cover more bouyant.

A water impervious cover for an arm cast is constructed in the same manner as the cover for the leg cast except that the shell is shaped to fit over a person's arm and the closed end of the shell is shaped to fit over a person's hand. Two or three inches of arm area must be available beyond the arm cast to assure a proper seal between the shell and the skin.

I claim:

1. A water impervious cover for an arm cast or leg cast, comprising:
 a shell consisting of a flexible, water impervious material that is shaped to fit over a portion of an arm or leg that has a cast secured thereto, the shell having a closed end that is shaped to fit over the extremity of said arm or leg, and an open end opposite thereto, wherein when the open end of the shell extends beyond the cast and the shell is tightly secured to the skin of said arm or leg beyond the cast, a pressure seal is created between the shell and said skin;
 an inflation valve communicating through the shell for enabling the air pressure inside the shell when the shell is fitted over said arm or leg and the shell is tightly secured to said skin beyond the cast, to be increased to thereby reinforce said pressure seal; and
 a layer of fabric on the exterior surface of the water impervious material of the shell for providing resistence to slippage when the exterior of the cover is wet.

2. A water impervious cover according to claim 1, wherein the fabric comprises nylon.

3. A water impervious cover according to claim 1, wherein the exterior region of the water impervious material of the shell near the open end is not covered by the layer of fabric.

4. A water impervious cover according to claim 3, further comprising strap means for wrapping around the shell in the uncovered region near the open end to tightly secure the shell to said skin at the open end.

5. A water impervious cover for an arm cast or leg cast, comprising:
 a shell consisting of a flexible water impervious material that is shaped to fit over a portion of an arm or leg that has a cast secured thereto, the shell having an open end, wherein when said open end of the shell extends beyond the cast and the shell is tightly secured to the skin of said arm or leg beyond the cast, a pressure seal is created between the shell and said skin;
 an inflation valve communicating through the shell for enabling the air pressure inside the shell when the shell is fitted over a said arm or leg and the shell is tightly secured to said skin beyond the cast, to be increased to thereby reinforce said pressure seal; and
 a layer of fabric on the exterior surface of the water impervious material of the shell for providing resistance to slippage when the exterior of the cover is wet.

6. A water impervious according to claim 5, wherein the exterior region of the water impervious material of the shell near the open end is not covered by the layer of fabric.

7. A water impervious cover according to claim 6, further comprising strap means for wrapping around the shell in the uncovered region near the open end to tightly secure the shell to said skin at the open end.

8. A water impervious cover according to claim 5, wherein the fabric comprises nylon.

* * * * *